United States Patent [19]

Yokoyama et al.

[11] Patent Number: 4,868,292

[45] Date of Patent: Sep. 19, 1989

[54] PREPARATION OF MONOSIALOGANGLIOSIDE

[75] Inventors: Tatsuro Yokoyama; Haruki Mori; Masanobu Arita; Atsushi Kojima, all of Yokohama, Japan

[73] Assignee: Mitsui Toatsu Chemicals, Incorporated, Tokyo, Japan

[21] Appl. No.: 888,183

[22] Filed: Jul. 22, 1986

[30] Foreign Application Priority Data

Jul. 31, 1985 [JP] Japan .............................. 60-167385

[51] Int. Cl.⁴ .............................. C08B 37/00
[52] U.S. Cl. .................... 536/18.5; 536/124; 536/127; 536/4.1
[58] Field of Search ............ 536/18.5, 4.1, 18.6, 536/124, 125, 127

[56] References Cited

U.S. PATENT DOCUMENTS

| | | | |
|---|---|---|---|
| 2,929,764 | 3/1960 | Hultin et al. | 536/18.6 |
| 4,454,315 | 6/1984 | Sasaki et al. | 536/123 |
| 4,521,593 | 6/1985 | Martin | 536/124 |
| 4,593,091 | 6/1986 | Della Valle et al. | 536/123 |
| 4,728,641 | 3/1988 | Tubaro et al. | 514/54 |

OTHER PUBLICATIONS

Ando, S. et al., Journal of Biological Chemistry 254:23 12224–9 (1979).

Lundblad, A. et al., European Journal of Biochemistry 104:323–330 (1980).

Leffler, H. et al., FEMS Microbiology Letters 8:127–134 (1980).

*Primary Examiner*—Ronald W. Griffin
*Assistant Examiner*—Nancy S. Carson
*Attorney, Agent, or Firm*—Millen, White & Zelano

[57] ABSTRACT

Monosialoganglioside is prepared by heating ganglioside at a temperature higher than 50° C. in a liquid medium containing water.

9 Claims, No Drawings

PREPARATION OF MONOSIALOGANGLIOSIDE

BACKGROUND OF THE INVENTION

1. Field of the Invention:

This invention relates to a process for preparing monosialganglioside.

A ganglioside is a member of a class of glycosphingolipids found abundantly in human and animal brains and is represented by the following general formula:

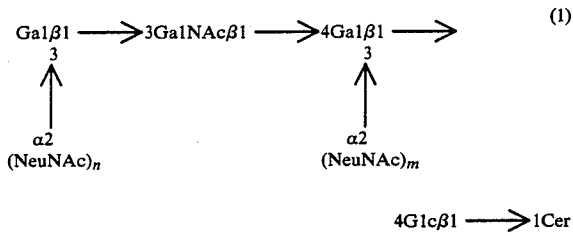

wherein GalNAc means N-acetylgalactosamine, Gal denotes galactose, Glc stands for glucose, NeuNAc is N-acetyl- and/or N-glycolylneuraminic acid (hereinafter called simply "sialic acid"), Cer denotes ceramide, n means an integer from 0–3, and m stands for an integer from 1–3. Depending on the number and bound position or positions of sialic acid residue or residues which are one of its components, there are many molecular species. Therefore, the term "ganglioside" as used herein is a general designation for these compounds.

Ganglioside may be roughly classified, depending on the number of sialic acid residue or residues bound per molecule, into monosialoganglioside (GM), disialoganglioside (GD), trisialoganglioside (GT), and tetrasialoganglioside (GQ) in which four sialic acid residues are bound. They can be classified further depending on the position or positions of the sialic acid residue or residues bound. The following molecular species of ganglioside are known: $GM_1$ [n=0, m=1 in the general formula (1)] as GM, $GD_{1a}$ (n=1, m=1) and $GD_{1b}$ (n=o, m=2) as GD, $GT_{1b}$ (n=1, m=2) as GT, and $GQ_{1b}$ (n=2, m=2) as GQ, etc.

The subscript of $GM_1$ means that all of the four saccharides of the basic oligosaccharide are present. The oligosaccharide formed by elimination of the end Gal from $GM_1$ is called "$GM_2$", and the oligosaccharide obtained by further elimination of GalNAc is called "$GM_3$".

The saccharide formed by complete elimination of the sialic acid residue is called asialo $GM_1$ or $GA_1$.

The action of ganglioside in living bodies has been being elucidated in recent years. It has been reported that $GM_1$ is effective for the repair and treatment of disorders of central and peripheral nervous systems [for example, Acta Neuropathologica, 62, 46–50 (1983); Agnati, L. F., et al., Acta Physiolgica Scandinavica, 119, 347–363 (1983)].

In Italy, a $GM_1$-containing ganglioside mixture with the name of "Cronacial ®" is marketed as a therapeutic drug for peripheral nerve diseases. An application for patent has been filed on this mixture (now Japanese Patent Laid-Open No. 34912/1977).

2. Description of the Prior Art:

As a conventional process for the formation of $GM_1$ from a ganglioside species other than $GM_1$, it has been known to cause neuraminidase, a desialidase, to act on the ganglioside species [for example, Richard Kuhn, et al., Chemische Berichte, 96, 866 (1963)].

It has also been reported that $GM_1$ was formed without using any enzyme [S. Ando, et al., The Journal of Biological Chemistry, 254(23). 12224–12229 (1979)]. Namely, it has been reported that a mixture of $GT_{1a}$, $GT_{1b}$, $GD_{1b}$, $GD_{1a}$ and $GM_1$ was obtained by holding GQ at pH 3 and 80° C. for 30 minutes in an aqueous solution of formic acid. According to the thin-layer chromatogram in this report, the proportion of $GM_1$ in the thus-obtained mixture is however extremely small and a further confirmation is hence necessary as to the formation of $GM_1$.

It has also been known that the sialic acid residue or residues of ganglioside are eliminated by acidolysis [for example, E. Klenk, Hoppe-Seyler's -Zeitschrift für Physiologische Chemie, 270, 185(1941); and L. Svennerholm, et al., The Journal of Biological Chemistry, 248, 740(1973)].

These prior art processes are intended to eliminate all sialic acid and the reaction products are $GA_1$ and neutral glycosphingolipids formed by elimination of 1–3 saccharides from the basic oligosaccharide. They are not intended to form $GM_1$.

As ganglioside supply sources employed presently in the industry, brains of bovine, swine and the like are used. Ganglioside available from these brains generally contains molecular species of ganglioside other than $GM_1$ in higher proportions than $GM_1$. The present inventors obtained ganglioside in a purified form by a process known per se in the art, namely, by dehydrating bovine brain with acetone, extracting it with a mixed solvent of chloroform, methanol and water by the process proposed by Svennerholm, et al. [Biochemical et Biophysica Acta, 617, 97–109(1980)], converting the extract into an aqueous solution of ganglioside by the Folch's distribution [J. Folch, The Journal of Biological Chemistry", 226, 497–509 (1957)], purifying it by DEAE-Sephadex-A25 [R. W. Ledeen, et al., Journal of Neurochemistry, 21, 829 (1973)], followed by a silica gel column fractionation. The composition of the above-purified ganglioside was 14% of $GM_1$, 45% of $GD_{1a}$, 10% of $GD_{1b}$, 22% of $GT_{1b}$ and 2% of $GQ_{1b}$.

In the above-described ganglioside preparation, "Cronacial ®", the content of $GM_1$ is 21% according to the literature for the preparation. If the molecular species of ganglioside other than $GM_1$ in the ganglioside mixture can be converted to $GM_1$, the effective component can be obtained in a correspondingly higher proportion. Although $GM_1$ can be formed by causing neuraminidase to act on ganglioside, this enzyme is expensive and therefore this process does not appear to be practical process from the economical standpoint.

SUMMARY OF THE INVENTION

The present inventors carried out a comparative investigation on the hydrolyzability of various molecular species of ganglioside and ganglioside mixtures. As a result, we found that the susceptibility to hydrolysis differs from one molecular species to another.

Namely, the reaction velocity from $GD_{1a}$ to $GM_1$ and that from $GM_1$ to $GA_1$ are different although they are the same in that one sialic acid is eliminated from the molecule in each of the reactions. It was found that the reaction velocity from $GD_{1a}$ to $GM_1$ is fast while the reaction velocity from $GM_1$ to $GA_1$ is slow.

Similar results were also observed with respect to another molecular species ($GT_{1b}$) of ganglioside.

The present inventors then investigated conditions for the hydrolysis in more detail. As a result, hydrolytic conditions under which molecular species of ganglioside other than $GM_1$ are subjected to hydrolysis and hence converted to $GM_1$ but $GM_1$ remains rather unaffected have been found, thereby leading to completion of this invention.

Namely, it has been uncovered that $GM_1$ is formed at a high conversion rate when a solution of ganglioside is added with an acid whenever necessary and is then heated to a suitable temperature at pH 3.5–7.

According to the process of this invention, more than 50% of molecular species of ganglioside other than $GM_1$ can be converted to $GM_1$, which has high utility as medicines, by the simple process in which a solution of ganglioside is heated subsequent to pH adjustment. The process of this invention is therefore an effective process for the preparation of $GM_1$.

The above and other objects, features and advantages of the present invention will become apparent from the following description and the appended claims.

DETAILED DESCRIPTION OF THE INVENTION AND PREFERRED EMBODIMENTS

The process of this invention will hereinafter be described in detail.

The ganglioside usable suitably as a raw material for the preparation of $GM_1$ is gangliotetraose-type ganglioside. The other molecular species of ganglioside are not considered to be fully suitable but no problem or inconvenience is encountered even if they are mixed.

As molecular species of ganglioside useful as raw materials in the practice of this invention, may be mentioned molecular species of ganglioside in which two or more sialic acid residues are bound per molecule of gangliotetraose, mixtures of such molecular species of ganglioside, ganglioside mixtures of the aforementioned mixtures and $GM_1$ mixed therein, crude ganglioside containing these molecular species of ganglioside at lower contents, and so on.

First, these molecular species of ganglioside are dissolved in a solvent. Although water is most suitable as the solvent, water containing an organic solvent e.g., methanol, ethanol, isopropanol, tetrahydrofuran, dimethylsulfoxide, chloroform or the like, may be used either singly or in combination. It is usually preferable to use water as the solvent but when the starting ganglioside is crude and has low solubility in water, preferable results may be obtained when an organic solvent is used.

An acid is then added to the ganglioside solution to adjust its pH to 3.5–7 if necessary. As an exemplary acid useful here may be mentioned an organic acid such as formic acid, acetic acid or propionic acid or a mineral acid such as hydrochloric acid, sulfuric acid or phosphoric acid.

When an alkali metal salt such as sodium or potassium salt or alkaline earth metal salt such as calcium or barium salt of crude ganglioside is used as a raw material, an acid is added to its solution in order to adjust the pH of the solution to a predetermined level.

However, when ganglioside purified by adsorbing ganglioside on an anionic ion exchange resin and then eluting it with ammonium acetate or ammonium salt type ganglioside obtained by treating ganglioside with a cation exchange resin ($NH^4$ type) is employed as a raw material, the pH of its solution is substantially neutral, that is, is in the range of 6–7. It is hence unnecessary to add any acid.

It is preferable to conduct the reaction at a lower temperature when it is carried out at a low pH at a higher temperature when it is carried out at a higher pH. It is necessary to heat to a temperature higher than 50° C.

The pH of the reaction mixture drops as the reaction proceeds. When the pH is adjusted to a lower level, the amount of this pH drop is smaller. It is however preferable that the pH does not drop beyond 3.5 during the reaction. An alkali can be added to avoid any excess drop of the pH when necessary. The heating time may range from 30 minutes up to 30 hours, usually, from 1 hour to 15 hours.

The progress of the reaction and the control of reaction products are conducted in the following manner.

A reaction mixture and a purified standard molecular species of ganglioside, each, in a predetermined amount are developed by a thin-layer chromatograph and after coloring them with the resorcinol reagent, they are measured by a Two-Wavelength chromatoscanner so as to determine their quantities [Seitaimaku Jikkenho (Vital Membrane Experimentation Procedures), Vol. I, Special Edition of "Tanpaku, Kakusan, Koso (Proteins, Nucleic Acids and Enzymes", The Kyoritsu Publishing Co., Ltd., 205(1974)].

When suitable conditions are chosen for the hydrolysis, about 65% of the molecular species of the starting ganglioside other than $GM_1$ are converted to $GM_1$.

After completion of the hydrolysis, the reaction mixture is neutralized with aqueous ammonia and $GM_1$ is then fractionated and purified by a known method [for example, Momoi, et al., Biochimica et Biophysica Acta, 441, 448–497(1976)]. Namely, the neutralized reaction mixture is caused to pass through a DEAE-Sephadex A25 ($CH_3COO^-$ type) column and then eluted with 0.05N ammonium acetate/methanol. After dialyzing and desalting $GM_1$ fractions, it is purified further through a silicic acid (Iatrobeads) column to obtain $GM_1$. The yield reaches as high as 50–54% of theoretical.

EXAMPLE 1

6.0 g of the sodium salt of a ganglioside mixture obtained from bovine brain and containing 14% of $GM_1$ was dissolved in 188 ml. of water followed by an addition of 12 ml of 0.1N acetic acid. The pH of the resulting solution was 4.81.

The solution was heated at 80° C. for 6 hours and then cooled. Its pH was 4.31. As a result of an analysis of the reaction mixture, the amount of $GM_1$ was found to have increased to 3.7 times compared to its amount before the reaction.

The reaction mixture was neutralized with 0.1N aqueous ammonia and then caused to pass through a 600 ml column of DEAE-Sephadex A-25 ($CH_3COO^-$). Water (1 l), methanol (1.5 l), chloroform-methanol (1:1) (0.7 l) and methanol (1 l) were passed successively through the column and the column was then eluted with 2 l of a 0.05N methanol solution of ammonium acetate. $GM_1$ was eluted in the 500–1750 ml fractions of the eluate. These $GM_1$ fractions were concentrated to dryness, followed by dissolution in 150 ml of water. After dialyzing and desalting the resulting solution, it was concentrated to dryness. The dry weight was 3.2 g.

It was then taken up in 150 ml of chloroform-methanol-water (55:45:2) and then caused to flow through a column packed with 600 ml of silicic acid (Iatrobeads) and equilibrated with the same solvent. The column was subjected to gradient elution with 1 l of chloroform-methanol-water (55:45:2) and 1.25 of chloroform-methanol-water (10:90:2). The resulting $GM_1$ fractions were concentrated to dryness.

The residue was dissolved in a small amount of chloroform-methanol (2:1), followed by an addition of 300 ml of acetone. The resultant solution was ice cooled and then treated in the same manner as in Example 1, thereby obtaining 450 mg of $GM_1$.

EXAMPLE 5

In the same manner as in Example 4, reactions were conducted by using hydrochloric acid, sulfuric acid, formic acid and acetic acid. The resulting reaction mixtures were analyzed. Test results are shown in Table 1.

TABLE 1

| Acid | Adjusted pH before heating | Heating Temperature (°C.) | Time (hrs) | Amount of $GM_1$ formed in terms relative to that before the heating |
|---|---|---|---|---|
| Hydrochloric acid | 4.5 | 100 | 0.5 | 3.8 |
| Sulfuric acid | 6.47 | 100 | 4 | 3.6 |
| Formic acid | 6.27 | 100 | 2 | 3.6 |
| " | 4.26 | 100 | 0.5 | 3.2 |
| Acetic acid | 6.36 | 100 | 4 | 4.2 |
| " | 3.96 | 80 | 0.5 | 4.0 | the resulting crystals were collected by centrifugation. After removal of the supernatant, the crystals were dried to obtain 2.65 g of $GM_1$.

EXAMPLE 2

In 400 ml of water, 800 mg of the ammonium salt (purity: 99% or higher) of $GD_{1a}$ was dissolved. The pH of the resulting solution was 6.17. The solution was heated at 100° C. for 5 hours. According to analysis of the reaction mixture, $GM_1$ was formed in an amount of 66% of its stoichiometric amount. The reaction solution was treated in the same manner as in Example 1 to isolate and purify $GM_1$, thereby obtaining 360 mg of $GM_1$ (yield: 54%).

EXAMPLE 3

One gram of the sodium salt of a ganglioside mixture containing 14% of $GM_1$ was dissolved in 100 ml of water and the resulting solution was caused to flow over a 2 hour period through a column packed with 10 ml of an ion exchange resin, "Amberlyst 15 ($NH_4^+$) type). The resin was washed with 200 ml of water. The column effluent and washing were combined together and then diluted to a total volume of 500 ml to prepare an aqueous solution of the ammonium salt of ganglioside. This solution has a pH of 6.66.

The solution was heated at 80° C. for 8 hours and the reaction mixture was analyzed. As a result, the amount of $GM_1$ was found to have increased to 3.6 times the amount present before the reaction. The pH of the reaction mixture was 4.46. In the same manner as in Example 1, the reaction solution was isolated and purified to obtain 432 mg of $GM_1$.

EXAMPLE 4

One gram of the sodium salt of a ganglioside mixture containing 14% of $GM_1$ was dissolved in 400 ml of water, followed by an addition of dilute hydrochloric acid to adjust its pH to about 6.5. Water was then added to bring the total volume to 500 ml. The resulting solution, the pH of which was found to be 6.47, was heated at 100° C. for 2 hours. As a result of an analysis of the reaction mixture, the amount of $GM_1$ was found to have increased to 4.0 times the amount present before the reaction. Its pH was 5.61. The reaction mixture was

EXAMPLE 6

Two hundred milligrams of the ammonium salt of $GD_{1a}$ were added to 100 ml of methanol having a water content of 0.2%, followed by heating at 100° C. for 8 hours in an autoclave. As a result of an analysis of the reaction mixture, $GM_1$ was found to have been formed in an amount of 70% of its stoichiometric yield.

EXAMPLE 7

Two hundred milligrams of the ammonium salt of $GD_{1a}$ were added to 100 ml of methanol containing $10^{-4}$ mole of acetic acid and having a water content of 0.2%, followed by their reaction at 100° C. in an autoclave. The reaction mixture was sampled periodically to analyze the amount of $GM_1$ formed in terms of its proportion (%) to its stoichiometric yield.

TABLE 2

| Reaction time (hrs) | Proportion (%) of $GM_1$ formed |
|---|---|
| 1 | 35 |
| 3 | 59 |
| 5 | 63 |
| 8 | 64 |

EXAMPLE 8

Two hundred milligrams of the sodium salt of ganglioside containing 14% of $GM_1$ were added to a 6:4:1 mixture of chloroform, methanol and water, containing $10^{-5}$ of acetic acid. The mixture reacted at 100° C. for 8 hours in an autoclave. As a result of an analysis of the reaction mixture, the amount of $GM_1$ was found to have increased to 4.6 times its amount before the reaction.

COMPARATIVE EXAMPLE

Two hundred milligrams of the ammonium salt of $GD_{1a}$ were dissolved in 100 ml of 0.01N formic acid. The resulting solution, the pH of which was 3.13, was heated at 100° C. for 80 minutes. As a result of an analysis of the reaction mixture, the amount of the starting material $GD_{1a}$ still remaining in the reaction mixture was on the order of trace amount and the amount of $GM_1$ formed was as little as 7% of its stoichiometric yield. A thin-layer chromatogram of the reaction mixture was color developed with orcinol reagent. A number of spots were observed but the principal reaction products were neutral glycolipids having no sialic acid residues such as $GA_1$.

Having now fully described the invention, it will be apparent to one of ordinary skill in the art that many changes and modifications can be made thereto without departing from the spirit or scope of the invention as set forth herein.

What is claimed is:

1. A process for increasing the monosialoganglioside ($GM_1$) content of a naturally occurring ganglioside, which comprises heating the naturally occurring ganglioside at a temperature of about 80°–100° C. in an aqueous liquid medium at a pH from 3.5 to 7 for a period of time effective to increase the $GM_1$ content thereof from about 3.2–4.2 times.

2. The process as claimed in claim 1, wherein the liquid medium contains an alcohol, chloroform or mixture thereof.

3. The process as claimed in claim 2, wherein the alcohol is methanol.

4. The process as claimed in claim 1, wherein the ganglioside is heated at a pH of about 4 to about 6.5.

5. The process as claimed in claim 1, wherein the starting ganglioside is in the form of an alkali metal, or alkaline earth salt and the pH of the liquid medium is adjusted with acid prior to heating the ganglioside.

6. The process as claimed in claim 1, wherein the starting ganglioside is in the form of the ammonium salt thereof.

7. The process as claimed in claim 1, wherein the ganglioside is heated at 80°–100° C. at a pH of about 4 to about 6.5.

8. A process for the production of the $GM_1$ species of ganglioside which comprises the steps of (a) heating ganglioside at a temperature higher than 50° C. for a period of time effective to hydrolize sialic acid groups from other glycosphingolipids present in the ganglioside and (b) isolating the thus produced $GM_1$ from the reaction product in an amount increased from about 3.2–4.2 times.

9. A process for the production of the $GM_1$ species of ganglioside which comprises the steps of (a) heating a naturally occurring ganglioside in an aqueous liquid medium for a period of time effective to hydrolyze sialic acid groups from glycosphingolipids other than $GM_1$ present in the ganglioside and (b) isolating the thus produced $GM_1$ from the reaction product, wherein the aqueous liquid medium is heated at a temperature of about 80°–100° C. for a period of time from about 0.5 to 4 hours effective to increase the $GM_1$ content thereof from about 3.2–4.2 times, and the pH of the aqueous liquid medium is maintained above pH 3.5 at least until after the temperature thereof is cooled to below 50° C.

* * * * *